United States Patent [19]

Blumenthal et al.

[11] Patent Number: 5,055,410
[45] Date of Patent: Oct. 8, 1991

[54] METHOD AND APPARATUS FOR DETERMINING NON-TRIGLYCERIDES IN OILS

[75] Inventors: Michael M. Blumenthal, Metuchen, N.J.; Jerry R. Stockler, Wantagh, N.Y.; Harry M. Van Tassell, Watchung, N.J.

[73] Assignee: Libra Laboratories, Inc., Piscataway, N.J.

[21] Appl. No.: 318,113

[22] Filed: Mar. 2, 1989

[51] Int. Cl.$^5$ ............................................. G01N 33/03
[52] U.S. Cl. ..................................... 436/60; 436/164; 436/20; 436/178; 422/61
[58] Field of Search ................... 436/60, 61, 164, 178, 436/20; 422/61, 75; 356/70, 36

[56] References Cited

U.S. PATENT DOCUMENTS

3,580,704  5/1971  Pickup et al. ......................... 23/230
4,349,353  9/1982  Blumenthal et al. ................. 23/230
4,654,309  3/1987  Mlinar et al. .......................... 436/61
4,731,332  3/1988  Blumenthal et al. ................. 436/61

Primary Examiner—Robert J. Warden
Assistant Examiner—Lyle Alfandary-Alexander
Attorney, Agent, or Firm—Lerner, David, Littenberg, Krumholz & Mentlik

[57] ABSTRACT

A method and diagnostic test unit for the determination of one or more non-triglycerides in an oil using an oil-miscible test solution prepared from an oil-miscible vehicle of monoglycerides, diglycerides or mixtures thereof and an indicator deliverable in admixture with the vehicle for assaying the non-triglycerides, wherein the indicator in combination with the non-triglycerides forms a reaction product characteristic of the amount of the non-triglycerides, and the indicator and vehicle are present in quantities and at a pH effective to provide detectable quantities of reaction product. The reaction product development is compared to a known standard to determine the presence or amount of the non-triglycerides in the oil.

59 Claims, 1 Drawing Sheet

METHOD AND APPARATUS FOR DETERMINING NON-TRIGLYCERIDES IN OILS

BACKGROUND OF THE INVENTION

The present invention relates to a method for evaluating hydrocarbon and olefinic materials and apparatus for performing the evaluations. In particular, the present invention relates to a method and apparatus for determining non-triglycerides in edible oils and fats or oil and fat substitutes.

Edible oils and fats and substitutes therefor are commonly used by food processors, food service establishments and in the home as a food ingredient and as non-aqueous cooking media in which foods are fried. The group of fats and oils suitable for use as food ingredients are known as salad oils. The group of fats and oils suitable for use as cooking media are known as cooking oils.

Salad oils and cooking oils are directed to a variety of end uses that may require incoming inspection of the salad or cooking oil, in-use examination of the oil for control and evaluation of conformity to manufacturing or regulatory specifications, or of suitability for continued use or reprocessing.

Salad oils are primarily applied to end uses in which the salad oil is consumed directly or as part of a food formulation, in which the salad oil is not subjected to substantial heating or oxidative conditions. Cooking oils, on the other hand, are incorporated into food as a secondary effect of their being used as a heat transfer medium. Depending upon the end use, cooking oils may be used only once, such as skillet oils, and thereby receive a limited exposure to heat and oxidative conditions, or the cooking oil may be repeatedly reused, such as deep frying oils, which receive prolonged heating and oxidative exposure.

Salad and cooking oils contain or acquire a variety of non-triglyceride constituents and/or contaminants, the importance of which depend upon the particular end use of the oil. The oils may contain minor constituents from the original plant or animal tissues from which the oils were produced, such as chlorophyll or myogolobin residues. The oils may contain contaminants which are residual from the original production of the fresh oil, including desirable processing additives such as anti-oxidants, anti-foamers and crystal inhibitors and the like, as well as adulterants that may be a residual processing additive undesirable in the finished product, or a material deliberately added contrary to local regulations to dilute an expensive oil or improve the end use properties of a cheaper oil. The oil may also contain degradation products resulting from production conditions. At the end use, upon application of the oil to the food, contaminants and intentional and unintentional adulterants tend to accumulate from contact of the oil with the food and process environment. Additives may be lost by attrition. Interaction products form as a result of the reaction between and among degradation products of the oil, and with fresh oil, and introduced food materials.

Oil processors, food processors, large volume food service establishments and regulatory agencies presently employ subjective and objective techniques to perform inspections of salad and cooking oils at the site of production and consumption. The oil may be subjected to an incoming inspection to confirm the nature of the triglyceride delivered and evaluate the nature of minor constituents, contaminants, additives, adulterants and degradation products. The oil may also be subjected to in-use examination for control and evaluation of the major constituents, minor constituents, contaminants, additives, adulterants, degradation products and interaction products for conformity to manufacturing and regulatory specifications and suitability of the oil for continued use or reprocessing.

Incoming oils are inspected for level of hydrolysis, determined by measuring free fatty acid content; heat history, evaluated by color determination, which is correlative to the formation of polymeric and other condensation products; and level of oxidation, which is determined by measurement of peroxide levels, an oxidatively produced species. Incoming oils are also evaluated for their triglyceride composition, minor constituents and processing residues. The above parameters are measured for conformity to the end user's specification. Additionally, the odor and taste of incoming oils are subjectively evaluated to determine rancidity, often without reference to a control standard.

If oils such as salad oils and fresh cooking oils are in conformity with incoming inspection specifications, they are then placed in in-use bulk storage until consumed and are subjected to conditions which promote oxidation, reversion to undesirable colors and flavors, and contamination. Used cooking oils are subject to the above conditions and in addition to the formation of interaction products of the reaction between oil degradation products with fresh oil, and introduced food materials, which exceptionally increase with prolonged use. This is a concern of the end user and has a direct effect upon product shelf life, production efficiency and conformity with regulatory specifications. Extracted cooking or salad oils from foods can be tested for their properties for quality control or quality assurance purposes.

With respect to salad oils and fresh cooking oils, end use conditions promote the formation of volatile or non-volatile species, primarily free fatty acids (FFA), oxidatively produced species, and colored species. Examination of the oil for control and evaluation for conformity to manufacturing or regulatory specifications or for suitability for continued use or reprocessing can be determined by measurement of one or more of these and other species.

Once formulated, other constituents of the finished product can react with the oil to produce interaction products, primarily oxidatively produced species and condensation products which can be extracted from food products and tested for quality control or quality assurance purposes.

With respect to used cooking oils, as an oil is repeatedly used in frying, it continuously degrades in composition at the oil-water interface near the surface of the cooking food to form surfactant chemicals, hydrolytic products such as FFA, interaction products resulting from reactions with food constituents, and oil degradation products. The interaction products include oxidatively produced species and condensation products including nitrogen and sulfur containing compounds from the reaction of oil and food proteins or carmelized materials in the presence of water evolved from the frying food. The oil degradation products include condensation materials such as polymers and colored materials. The FFA combine with metals leached from food tissues and coatings, residual water hardness from sanitation activities and food ingredients to form soaps, a type of surfactant. At first the surfactants promote heat transfer at the oil-water interface at the food surface. However, with continued use, the oil further deteriorates until the surfactant chemicals reach a level at which the oil-water interfacial tension is lowered to a point where the oil interpenetrates the steam envelope from the cooking food and soaks into the food causing excessive water loss from the food surface, darkening and hardening. The oil also foams at its interface with the air, resulting in oxygen incorporation and accelerated oxidative degradation of the oil. The water loss from the food surface additionally inhibits heat penetration to the core of the food by creating a hard crust with a low thermal conductivity. Further, increased surfactant levels cause the oil to adhere to heater surfaces, which causes the oil to coke on the surfaces, thus generating colored materials and an insulating coating over the heater element surfaces, which can contribute to loss of control in a temperature versus energy process control system.

Therefore, it is desirable to maintain the surfactant level of the cooking oil within a range at which heat transfer is optimized. Once this limit is exceeded, surfactant levels may be lowered by dilution with fresh oil, by various filter aids or treatments, or the oil may be simply discarded. Therefore, it is desirable that cooking oils be routinely tested for soap or other surfactant species to determine whether an oil should be diluted, treated or discarded.

The level of soap present correlates with the general level of water-activated surfactants present and measurement of the amount of soap present in fat provides an accurate indication of the total water-activated surfactant level. The amount of soap can be determined by measuring the relative basicity of a fat sample with an alkaline indicator.

The polymers are thermal or oxygen condensation products associated with the heat history and foaming and other evidences of surfactancy of the oil and result from cross-linking of carbons from adjacent fatty acids whether free or on triglycerides or other fatty acid esters. These polymeric materials may be oxygenated or non-oxygenated and are associated with the surfactant phenomenon. Polymeric material levels may be measured by reagent indicators, the determination of which provides an indication of the in-use condition of the oil.

The majority of fatty acids free from triglycerides do not immediately form soaps, since metal ions are present in oils at the parts per million level while percentages of fatty acids are hydrolyzed from triglycerides. Oils at any given time therefore contain a certain quantity of FFA's, the levels of which correlate over a short range somewhat to the degree of degradation, although not as accurately as do measurements of soaps or total polar materials because the FFA's are intermediates in the formation of both. Stated another way, an FFA measurement is not a measurement of every FFA formed, because many FFA's further react to form soaps and other polar materials that are not detected in an FFA measurement. However, there is some utility in the determination of FFA levels, which are determined by measuring the available acidity of an oil sample with an acidic indicator.

The above species, and others present, are subclasses of non-triglycerides known as total polar materials (TPM) that form in salad and cooking oils. Many countries officially recognize TPM measurement by column chromatography as a regulatory analysis for cooking and salad oil. The previously mentioned FFA's, soaps, colored materials, polymers, degradation products, interaction products, additives, adulterants and minor constituents, all of which are not triglycerides, are collectively determined essentially quantitatively by this test. This is in contrast to individual determinations of each species, which have utility but do not provide an overall picture of the state of the oil. Because of the breadth of the materials assayed, TPM measurements are often used by regulatory agencies and manufacturers as an initial screening of an oil sample to determine if additional specific testing is necessary. Occasionally, a non-polar material such as a degradative or contaminant species may be present in a chromatographically analyzed oil sample. It would be of interest if a quick test could be devised which included these non-polar, but perhaps nutritionally important species in its assay for quality of an oil.

Methods of measuring alkalinity, TPM's and FFA's in olefinic materials such as cooking oils, and test kits employing such methods are known. U.S. Pat. No. 3,580,704 discloses a colorimetric indicator for determining the pH of motor oil in which a test paper is treated with a pH indicator and a long chain non-ionic surface active agent containing hydroxy hydrophylic groups in which the indicator is soluble, preferably an alkylaryloxy polyalkoxyalkanol such as Triton X-100. A strip of the treated paper is dipped in the oil to measure its pH.

U.S. Pat. No. 4,654,309 discloses an article for measuring the acid content of cooking oils and fats, including FFA's in which a porous support is treated with a pH indicator and a humectant dihydroxy aliphatic polyethylene glycol solvent. The strip has one or more test areas treated with a predetermined quantity of base corresponding to a known quantity of acid which must be present to neutralize the base before a color change indicating the acid quantity will occur. The pH, and hence, the fatty acid content of the oil, is measured by dipping the paper in the oil and noting the presence or the absence of a color change. Such a test, however, is destructive of the oil sample measured and does not handle well in a later, secondary examination.

U.S. Pat. No. 4,349,353 discloses a method and composition for a determination of alkaline materials such as soaps in an oil using a test solution containing a pH indicator dye and a volatile solvent that is immiscible with the oil. The solvent is used to extract alkaline substances which then react with the pH indicator in the solvent, which indicator develops a color that can be compared to a known standard to determine the pH and accordingly the degree of alkalinity and soap content of a sample.

German Patent Nos. 2,543,543 and 2,630,052 disclose methods for determining the degree of oil oxidation by dissolving the oil in a volatile alkaline alcohol solvent containing a redox indicator such as bromthymol blue, bromcresol green, cresolindophenol, thymolindophenol, bromphenol blue, thymol blue, xylenol orange, bromcresol purple, methylene violet, methylene green or patent blue.

U.S. Pat. No. 4,731,332 discloses a method and a test kit for a determination of polar substances in oil using a test solution containing indicator dye and a volatile solvent that is immiscible with the oil. The solvent is used to extract polar compounds that react with the indicator to produce a visible or fluorescent color change that is compared to a known standard to determine the amount of polar substances in the oil.

Methods using test strips are disfavored because the oil sample measured is destroyed. While extraction tests may not be destructive of the oil sample, the tests fail to accurately assay those species that are not readily extractable into water. Furthermore, once in an aqueous environment, the FFA's and alkaline species tend to neutralize each other, thereby rendering tests of either somewhat inaccurate.

The solvents in the above patents, in addition to those that are volatile, can be toxic or flammable and can present a hazard when handled in a food environment. The solvents also present a disposal problem.

A non-destructive test method and test kit that did not involve destruction of the sample or solvent partitioning of the species to be measured would be highly desirable, especially a method and test kit that was safe, non-toxic and did not present a disposal problem.

SUMMARY OF THE INVENTION

A method for determining the amount of one or more non-triglycerides in an oil has now been discovered in which a single-phase non-toxic oil-miscible test solution is used. The method is performed by mixing a predetermined amount of the test solution with a predetermined amount of oil to be tested. According to the method of the present invention, the test solution includes an oil-miscible vehicle and an indicator deliverable in admixture with the vehicle for assaying a non-triglyceride contaminant or constituent of an oil such as soaps, FFA's, polymers, colored materials, or TPM's. Appropriate vehicles include monoglycerides, diglycerides and mixtures thereof, which are non-toxic and do not present a disposal problem. The indicator in combination with the oil constituent or contaminant to be assayed will provide a further reaction product characteristic of the presence and/or amount of the constituent or contaminant, such as, for example, a directly interpretable color change. The indicator and vehicle are present in amounts and at a pH effective to provide the detectable quantities of the reaction product, which is a function of the quantity of the constituent or contaminant present in the oil sample. The amount of such oil constituent or contaminant is determined by comparison of the reaction product to an external or internal standard capable of corresponding reaction product development to the amount of non-triglycerides in the oil.

According to the method of the present invention, a predetermined amount of the test solution is mixed with a predetermined amount of the oil to be assayed and agitated until a colored uniform homogeneous mixture is obtained. The reaction product is then allowed to develop in the mixture and the amount of non-triglycerides in the mixture is determined by comparing the reaction product development to a known standard. The test solution of the invention is entirely contained within the testing apparatus. Thus, the present invention can be utilized by non-skilled operators, and the results are provided in the form of a stable reaction product, such as a color change, that may be stored for subsequent evaluation.

According to the present invention, testing units are also provided for diagnosing the quality of oils by measuring constituents and contaminants. The diagnostic testing units include an oil-miscible test solution including a vehicle and an indicator soluble in the vehicle for measuring non-triglycerides such as soaps, FFA's polymers, colored materials or overall TPM's. Appropriate vehicles include monoglycerides, diglycerides and mixtures thereof. The indicator in combination with the oil contaminants or constituents to be assayed will provide a further reaction product in the test solution characteristic of the presence and/or amount of the contaminant or constituents such as, for example, a directly interpretable color change. The indicator and vehicle are present in amounts effective to provide detectable quantities of the reaction product, which is a function of the amount of the contaminant or constituent present in the oil sample. The diagnostic test units also include an external or internal reference standard capable of correlating the reaction product development to the amount of non-triglyceride contaminant or constituent in the oil sample assayed.

For convenience, the term "oil" is used in the present specification and claims to refer to fats which are solid at room temperature, to oils that are liquid at room temperature, substitutes therefor, and to any other lipid materials from other sources such as food stuffs, physiological fluids, and animal and vegetable tissues. The testing method and diagnostic test units are preferably used in testing fresh or used salad or cooking oils for non-triglyceride constituent or contaminant levels therein as a measure of the oils suitability for use, however, the testing method and diagnostic test unit of the present invention are also suitable for the determination of constituents and contaminants of motor oils, process oils and other hydrocarbon or olefinic substances.

The present invention is based upon the discovery that a broad range of indicators, believed only to function as reagent indicators in oil immiscible or oil-solvent systems, unexpectedly function in oil-miscible systems. While not being bound by any particular theory, it is believed that the indicators of the present invention either function in a polar environment, regardless of whether it is aqueous or non-aqueous, or that the water present as an oil contaminant or degradation product may be stabilized in a single micellular phase by the mono- and diglycerides, in which the micelles serve as reactive or interactive sites or species for the indicators.

DETAILED DESCRIPTION OF THE PREFERRED EMBODIMENT

The present invention is useful in the qualitative or quantitative determination of non-triglycerides present as contaminants or constituents in oils including cooking oils, salad oils and other hydrocarbon or olefinic substances. The method of the invention, and the diagnostic test units embodying same, employ an indicator, which, in combination with an oil contaminant or constituent, provides a reaction product evidencing the presence of the oil contaminant or constituent, which indicates the oxidative, degradative and/or contaminated state of the oil, or the presence of constituents associated with the oil in question. The contaminants or constituents in the oil sample measured by the process of the present invention include, for example, FFA's, soaps, colored materials, polymers, degradation products, interaction products, additives, adulterants, minor constituents and other among the TPM's.

The indicator may provide a color change as a reaction product, such as a chromogen, dye or pigment. The indicator may function mechanically to absorb and physically remove species from the test solution, leaving other species behind for detection. Such indicators include, for example, activated carbon, activated minerals, synthetic silica gels, molecular sizing materials, or ion exchange materials.

The indicator is preferably a material that produces a color change. The color change can be in the visible range or in the ultraviolet range. The indicator may be colorless to start with and develop a color upon exposure to an oil contaminant or constituent, or the indicator may be colored to start with and become colorless, or the indicator may be a light color and change to a deep or other distinctive color. The change of color in the ultraviolet range is determined by exposure of the test solution to ultraviolet light, to detect the color change of the solution from fluorescent to non-fluorescent or vice versa. The color change may also be a detectable shift in the ultraviolet spectrum.

Suitable indicators for use in the present invention include dyes such as bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol, FD&C Blue No. 1 (brilliant blue FCF), malachite green, FD&C Blue No. 2 (indigo carmine), FD&C Red 40 (Allura Red AC), methyl yellow, congo red, bromchlorophenol blue, chlorophenol red, and salts and lakes of the above dyes capable of preparation in such form, all of which may be located among lists of such indicators in vendor catalogs or technical compilations or data bases used by those of ordinary skill in the art. Suitable indicator dyes for the assay of TPM's include bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol, malachite green and FD&C Blue No. 1. Preferred dyes for the assay of TPM's are FD&C Blue No. 1, malachite green and bromcresol green.

An especially preferred indicator dye for the measurement of TPM's is FD&C Blue No. 1, the color of which is blue up to about 4% TPM, the color is then blue-green up to about 13% TPM, then the color is light green up to about 17% TPM. The color is then green up to about 24% TPM and olive green above 24% TPM when used according to the method of the present invention. What is particularly advantageous about these color properties is that 13% TPM is an upper limit preferred for TPM content of oils by salted snack food processors. The 17% TPM is an upper limit preferred for TPM content of oils by commercial food processors of fried coated meat, fish and poultry products. The 24% TPM is the TPM limit preferred by large volume food service establishments in their oil used for refrying of previously prepared food. In addition, 24% TPM is at or slightly below the maximum TPM permitted in oils for food processors and food service establishments by the regulatory agencies of many European governments.

Indicators suitable for the assay of FFA's can also be used to assay alkaline materials. The indicators are typically pH indicators that undergo a range of color changes at both alkaline and acid pH's. To assay an acid or acids, a slightly alkaline test solution is utilized so that the color of the indicator corresponds to the lower end of the alkaline range. The presence of FFA's, for example, in an oil sample shifts the pH of the test solution and the indicator color into the acid range with the degree of shift a function of the FFA concentration.

Similarly, to assay alkaline materials, a slightly acidic test solution is utilized so that the color of the indicator corresponds to the upper end of the acid range. The presence of alkaline materials in an oil sample shifts the pH of the test solution and the indicator color into the alkaline range, with the degree of shift a function of alkaline concentration.

The initial pH of the test solution may be adjusted if necessary to provide a slightly acidic or slightly alkaline test solution. Suitable alkaline materials for pH adjustment include sodium hydroxide, potassium hydroxide, triethanolamine, imidazole, and quarternary ammonium salts. Suitable acidic materials for pH adjustment include mineral acids such as hydrochloric, sulfuric or phosphoric acids or organic acids such as citric acid and the like. Additional quantities of alkali or acid materials may be added to raise or lower test solution pH so that the indicator of the test solution is less sensitive to FFA's or alkaline materials and can be utilized to assay higher concentrations of these analytes, respectively.

Suitable indicators for the assay of FFA or alkaline materials include bromphenol blue, bromcresol green, bromcresol purple, methyl yellow, congo red, bromchlorophenol blue, and chlorophenol red. The preferred dye is bromcresol green. The color changes of pH indicators in glyceride systems do not correspond to the performance of the indicators in aqueous systems and some testing will be necessary to confirm the pH levels at which indicator color changes occur. Such testing is not unduly burdensome and can be easily performed by one of ordinary skill in the art following the foregoing disclosure.

For example, if bromphenol blue is being employed as the indicator, to obtain a characteristic range of color change for the test solution when FFA's are present at high levels between about 7% and about 10%, the test solution must contain about 0.1% imidazole, an alkaline material. Without the alkaline imidazole, a test solution including bromphenol blue responds instead to alkaline species.

The test solution also includes a vehicle in which the oil to be tested is soluble and in which the indicator can be delivered in admixture. The indicator and vehicle should be present in relation to each other in amounts effective to provide detectable quantities of a reaction product as a function of the amount of contaminants or constituents in the oil, i.e., the test solution should contain an effective amount of the indicator relative to the vehicle to provide measurable quantities of a desired reaction product in response to amounts of oil contaminants or constituents to be assayed.

Suitable vehicles include oil miscible organic vehicles such as monoglycerides, diglycerides and mixtures thereof. Acceptable monoglycerides are glyceryl mono-oleate, glyceryl monostearate, glyceryl monolaurate and mixtures thereof. Preferred monoglycerides are glyceryl mono-oleate, glyceryl monostearate and mixtures thereof. A more preferred monoglyceride is glyceryl mono-oleate. Acceptable diglycerides are glyceryl dioleate, gylceryl distearate, glyceryl dilaurate and mixtures thereof. Preferred diglycerides are glyceryl dioleate, glyceryl distearate and mixtures thereof. A more preferred diglyceride is glyceryl distearate.

The particular monoglycerides and diglycerides, as well as the monoglyceride to diglyceride ratio utilized, can be selected to obtain a desired melting point as well as compatibility with the other reagents of the test solution used in the method of the present invention. The weight ratio of monoglyceride to diglyceride can be between about 0:100 and about 100:0. Preferably, the ratio is between about 3:1 and about 1:3. More preferably, the ratio is about 1:1.

However, any solvent that provides the characteristics described above would be suitable for use in the present process. The use of monoglycerides and diglycerides as the solvent for the test solution of the invention has been found to provide particularly advantageous results in terms of providing a stable non-toxic oil soluble test solution suitable for delivering an indicator in admixture that additionally presents no disposal problems.

It must be noted that mono- and di- glycerides from commercial sources vary in antioxidant, glyceride ester and acid/alkaline content. Mono- and di-glycerides for use in the present invention will require screening, perhaps from batch to batch, to determine what adjustments, if any, will be necessary to obtain a test solution of the desired pH. The acidity of a mono-or di- glyceride sample can be easily determined by one of ordinary skill in the art by following AOCS Ca5a-40. Alkalinity may be determinable by AOCS Cc17-79.

The present invention includes an analog colorimetric assay method in which the color change occurs gradually over a broad color range, the color or intensity of which is indicative of the amount of oil contaminant or constituent. The present invention also includes a digital colorimetric assay method in which the color change occurs sharply at a predetermined level of oil contaminant or constituent indicative of an amount of contaminant or constituent at about or exceeding this level. To obtain such a sharp color change, digital colorimetric assay methods utilize a chromogen that produces a rapid, sharp color change upon reacting with one molecule of analyte. Typical chromogens include dithiazone for the detection of specific metal ion contaminants.

Regardless of whether analyte concentration in the colorimetric assay method of the present invention is determined by the presence or degree of color changes, the test solution contains an effective amount of the indicator so that when a predetermined amount of the test solution is mixed with a predetermined amount of the oil sample, a sufficient color change is obtained when a characteristic amount of contaminants or constituents is present in the oil. Typically, the solution contains from about 0.001 to about 0.10 parts by weight of the indicator per 100 parts by weight of the test solution. When the indicator is malachite green a typical desirable range has been found to be about 0.002 to about 0.006 parts by weight of this dye for 100 parts by weight of the test solution.

In a preferred embodiment of the colorimetric assay method of the invention, an effective amount of the indicator is included in the test solution so that, when a predetermined amount of the test solution is mixed with the predetermined amount of an oil containing an amount of contaminants making the oil unsuitable for further cooking use, a sufficient visible color change occurs so that a quick and easy determination can be made to discard such used oil or treat it to remove such contaminants. The amount of indicator required to respond to those ranges of contaminant concentration that typically occur in used cooking oil samples to be tested can be readily determined from the foregoing disclosure by one of ordinary skill in the art. Included within such a range is the level of contaminant that, when present in used cooking oil, requires the oil to be discarded or treated. Thus sufficient relative amounts of vehicle and indicator are utilized so as to provide the most clearly distinguishable range of colors corresponding to different amounts of contaminant in an oil sample, and to provide a distinctive color change at about the level of contaminant that requires the oil to be discarded or treated.

The color changes of bromcresol purple and bromthymol blue are sensitive to elevated temperatures and should not be used in test solutions that will stabilize after mixing with the oil sample at temperatures in excess of 120° C. This temperature sensitivity, however, can be used advantageously. It has now been discovered that oils containing degradation product levels unsuitable for further cooking use upon exposure to microwave energy heat to temperatures in excess of 120° C., while oils that are suitable for continued use do not. The suitability of an oil for continued use may be quickly determined by mixing a predetermined amount of the oil with a predetermined amount of test solution containing bromcresol purple or bromthymol blue and exposing the resulting mixture to microwave energy for about one to five minutes. The development of a color change will indicate that the oil is unsuitable for continued use.

While the method and diagnostic testing kit of the invention is ordinarily used to directly assay an oil sample, the oil sample may first be reacted with a primary reagent, the product of which is then assayed by the test solution. The primary reagent may be included in the test solution and react with components of the oil sample to produce non-triglycerides to be assayed by the indicator. Typical primary reagents include lipid enzymes specific to a particular fatty acid, so that triglycerides identifiable by certain fatty acid groups can be detected in samples in which FFA's are not otherwise present. The lipase cleaves the fatty acid, if present, from the triglyceride making it available for detection as an acid. A positive FFA or acidity result then would indicate the presence of the particular triglyceride identifiable by the fatty acid and may suggest the origin of the oil sample. For example, lipase specific to lauric acid would cleave off lauric acid groups in the test solution from triglycerides containing same. If the oil sample had no triglycerides containing lauric acid, a negative FFA reading would result. Oil samples having triglycerides containing lauric acid, typical of tropical oils, would cleave off lauric acid in the test solution and provide a positive FFA reading that would indicate the presence of these triglycerides.

The present invention also contemplates the assay of non-triglycerides other than FFA's, alkalines and TPM's. For example, tocoquinone concentration can be measured spectrophotometrically using the oils in which this compound commonly occurs as the internal reference standard. Chlorophyll can be identified spectrophoto-metrically using FD&C Blue No. 1 as the internal dilution reference standard. Heavy metals can be identified by a visible color change using dithiazone as the indicator. Aldehydes and ketones can be identified by a visible color change after first reacting a sample with dinitrophenylhydrazine as a primary reagent and then using iodine or bromine as an indicator. Unsaturated materials can also be identified by a visible color change using iodine or bromine as an indicator, and peroxides can be identified by a visible color change using iodine as an indicator.

Gossypol concentration can be identified spectrophoto-metrically using FD&C Blue No. 1 as an internal dilution reference standard. Rancidity can be identified by a visible color change using phloroglucinol as an indicator. Water can be identified as by a visible color change using a suspension of fine anhydrous copper or cobalt salts as an indicator. Sodium, potassium, calcium, magnesium or other metal ions can be identified by a visible color change by using known quantities of FFA's as a primary reagent with an alkaline indicator for the detection of soaps formed. Iron can be identified by a visible color change by using tannic acid, dithiazone or gallic acid.

Proteins can be identified with an amino acid residue reagent indicator. Sucrose polyester fat substitute adulterants can be identified with a carbohydrate residue reagent indicator.

In most instances, the vehicle comprises most of the test solution except for the indicator, however, it should be pointed out that other materials can be present in the test solution.

One or more optional diluents may be added to the solvent to adjust the melting point, reaction rate, rate of crystallization and system solubility to desired levels. These diluents include other monoglycerides and glyceridic esters, as well as paraffinic oils such as mineral oils, lipids and other fatty materials, including hydrogenated and partially hydrogenated oils such as coconut oil, olive oil, palm oil, peanut oil, rapeseed oil, canola oil, riceseed oil, rice bran oil, soybean oil, cottonseed oil, sunflower oil, sesame oil, safflower oil, tallows, fish oils, poultry oils, fat replacers, and mixtures thereof. Natural or synthetic waxes can also serve as diluents, including paraffin wax, petrolatum, polyethylene glycol, polypropylene glycol, microcrystalline wax, beeswax, carnuba wax, candelilla wax, lanolin, bayberry wax, spermaceti, ricebran wax and combinations thereof. The diluents are also useful to provide opalesence, refractive properties, and to suspend the partially soluble ingredients or to encapsulate the ingredients, particularly the indicator.

The diluents are typically used to adjust the melting point of the test solution. When the test solution contains no diluent, the melting point is typically between about 30° C. and about 80° C., preferably between about 40° C. and about 75° C. and most preferably between about 50° C. and about 70° C. Lower melting point diluents such as mineral oils and crystal inhibitors can be used to depress the melting point of the test solution to temperatures as low as about 18° C. to provide a test solution that is fluid at room temperature. Higher melting point diluents can be added to raise the melting point of the test solution to provide a solution that is solid at room temperature and at elevated temperatures common to distribution conditions. This provides a product that is simple to transport over great distances. The elevated temperatures do not interfere with the method of the present invention since the test solution is usually mixed with a used cooking oil under process conditions exceeding 120° C.

The diagnostic testing units of the present invention are prepared by combining the test solution with a suitable physical support. The support member may be any material capable of bearing the system for exposure to the analyte, and preferably the support is inert to the reactants. Specific examples include sheets, rods, webs, filters, strip and containers such as vials or tubes, including capillary tubes, or other vessels. Suitable materials include glass, cellulose, wood, metal, textiles or polymerics such as polyethylene, polypropylene, polyacrylates, polycarbonates, polymeric fluorocarbons and the like. The test unit may be incorporated onto a material that is capable of taking up the analyte solution by capillary action such as a bibulous material or a capillary tube or other similar means. The capillary material should take up a set and reproducible amount of liquid. Bibulous materials include metal oxides, polymeric materials, hybrid polymeric/ceramics as well as cellulosics.

The preferred physical support is a polypropylene tube or vial capable of being mass produced to accommodate a set and reproducible amount of test solution and analyte sample. The tube can be filled volumetrically or to a mark. The preferred embodiment of the present invention utilizes a polypropylene tube containing the test solution and having a single fill line printed thereon indicative of the volume of oil sample appropriate for mixing with the test solution.

A number of sealants may be used in a variety of forms to cover one or more surfaces of the test solution and protect the surfaces from environmental conditions When the support is a polyprophylene tube, the interior of the tube together with the meniscus of the solution can be coated with the sealant to provide a barrier between the environment and the test solution. The sealant should be impermeable to gases and liquids that are capable of permeating through the polyprophylene tube, such as carbon dioxide, oxygen, and water at elevated temperatures. Typical sealants include paraffin wax, microcrystalline wax, natural waxes, synthetic polymers such as low molecular weight polyethylenes and the like, and higher molecular weight monoglycerides. A coating of acrylate can also be applied and crosslinked in situ using UV light.

The shelf life of certain diagnostic testing units of the present invention can be improved if the ingredients are segregated in separate vehicle layers prior to use. For example, in a testing unit using alkali sensitive dyes and an alkaline threshold reagent, it is preferable, but not necessary that both ingredients be maintained in separate vehicle layers separated by a sealant prior to use. The oil sample to be assayed would then be added at an elevated temperature sufficient to melt the sealant layer. This may be the temperature at which the oil sample is removed from the food process, or it may be necessary to heat the oil sample prior to combining it with the test solution. For temperature sensitive oils, the diagnostic test unit may be heated prior to testing. The physical form of the test solution at room temperature, may be liquid, solid or mixtures of both, e.g., a liquid encapsulated in a solid coating or matrix, or a liquid sealed into a physical support by a solid layer. Another form is that of a tablet or capsule, which may be stored separately from the physical support, and contacted with the physical support either just prior to the addition of an oil sample, or after the addition of the sample.

Inert fillers, binders, surfactants and the like can also be used in the test solution to promote adhesion of the system to the support and promote system miscibility. Adhesion of the test solution of the present invention to plastic supports can also be improved by corona discharge treatment of the plastic.

When the physical support is a polyprophylene tube, the support may be sealed with a cap such as a twist cap or a snap cap. Either cap may also contain a well in its interior to segregate an ingredient from other components of the test solution to improve the shelf life of the test solution. The closure may also be provided with a tamper-evident band or cover to insure the integrity of the test results. The tamper evident means could be applied after manufacture and prior to testing to ensure the quality of the test solution and it may be applied after the test is performed to protect the test results. The tamper evident means may also be used as an area for information or identification notation.

A diagnostic testing unit, when in the form of a tube or other vessel, may further include an agitation means to ensure thorough mixing of the test solution and the oil sample to be analyzed. Such agitation means include a plastic or glass bead, stainless steel ball, paddle and/or stir-rod or bar, magnetic stir-bar or ultrasonic susceptor. The agitation means may also be used to encapsulate one of the components of the invention, such as the indicator.

The method and diagnostic testing units of the present invention further include an internal or external reference standard for correlating the reaction product obtained with the oil constituent or contaminant assayed in a qualitative or quantitative manner. The digital colorimetric assay method of the present invention requires no reference standard because a sudden color change is provided at a predetermined concentration of analyte. The analog colorimetric method of the present invention further includes a color comparator. TPM determination methods include color comparators calibrated by reference to IUPAC-AOAC methods. Methods relying upon pH determinations include color comparators calibrated to standard solutions. The color comparators equate solution colors with analyte concentration.

The analyte concentration need not be indicated by color development. The test solution of the invention may include an internal reference standard, such as a dye, for spectrophotometric measurement of the oil sample, with the spectrum of the oil compared to the spectrum of the internal standard. This can provide an indication of the heat history, oxidation status and the presence or absence of contaminants or minor constituents in the oil sample. The spectral comparison can also be equated to analyte concentration.

It is contemplated that the color comparator or internal reference standard spectra can be incorporated into computer software and displayed onto a screen for comparison with test results.

The relative amounts of the test solution employed in the method of the invention depend upon a number of factors, including the concentration of the indicator in the test solution, the expected level of contaminants or constituents in the oil to be tested, and so forth. The ratio of test solution to oil sample will vary accordingly, typically between about 1:20 to about 1:1, test solution to oil sample, and from the foregoing disclosure can be readily determined by one of ordinary skill in the art.

The process of the invention is simple to perform, even for the relatively inexperienced personnel of fast food outlets and commercial food processor production lines. The test is performed by mixing a predetermined amount of test solution with a predetermined amount of the oil sample to be assayed. The oil solution and test solution are mixed on or within the support means. The support means is optionally covered or closed. The mixing is typically promoted with agitation by known mechanical means. The oil and test solution should be liquid, and if not, should be made liquid by contacting with a source of heat. The oil sample and test solution should be mixed until a uniform homogeneous mixture is obtained and production of the reaction product of the analyte and indicator is maximized. The analyte in the oil sample is then qualitatively or quantitatively assayed by comparison of the reaction product to the internal or external reference standard.

No special conditions other than as discussed above are necessary for performing the present invention. Thus, the process of the invention can be performed at ambient conditions. However, other conditions can be employed so long as they do not unexpectedly change the reaction product that would ordinarily be obtained by the predetermined amounts of test solution and oil sample.

As stated above, the analog colorimetric assay method of the present invention compares the color change developed to an external color standard which equates color development to analyte concentration. The external color standard is typically a color comparison card. In a preferred embodiment, the card is prepared from translucent inks printed onto a translucent material with both the ink and the material having light transmission properties equivalent to the light transmission properties of the testing solution and the support means of the diagnostic testing units. Both the card and the test solution are held up to the light adjacent to each other and compared. The comparison of light-transmitted colors rather than light-reflected colors eliminates inaccuracies introduced by the different reflective properties of the materials compared. The operator matches that portion of the card having a color closest to the color developed in the test solution. This color is then equated to analyte concentration in the manner described above.

Figure 1:
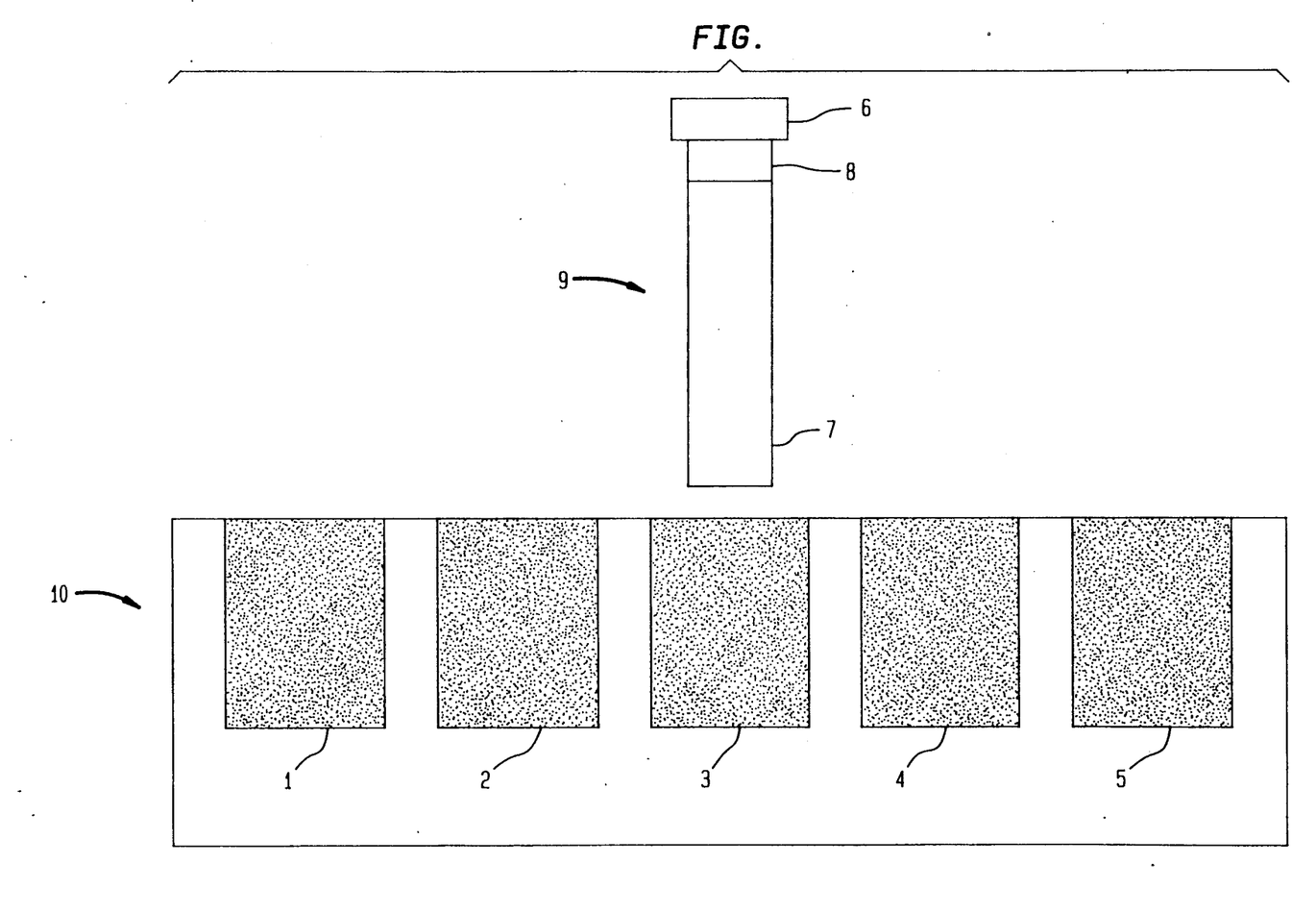
The sole FIGURE depicts a diagnostic testing unit adjacent to a color comparison card for color comparison purposes.

For example, referring to FIG. 1, a diagnostic testing unit 9 includes a polypropylene tube 7 sealed with a cap 6 with the tube having printed upon it a fill line 8. The tube contains an amount of test solution in a predetermined quantity that provides the proper ratio of test solution to oil sample when the tube is filled to the fill line 8 with the oil sample. Once the oil sample has been added to the test solution and mixed and maximum color development has occurred, the color developed is compared to color comparison card 10.

The card depicted provides results for the assay of TPM's with FD&C Blue No. 1 and color portions 1–5 are shown. Color portion 1 is blue and corresponds to TPM's below 5%. Color portion 2 is blue-green and corresponds to TPM's between about 5 and about 12%. Color portion 3 is light green and corresponds to TPM's between about 13 and about 16%. Color portion 4 is green and corresponds to TPM's between about 17 and about 23%. Color portion 5 is olive green and corresponds to TPM's of about 24% and above.

As shown in FIG. 1, the tube 9 in which the color change has been allowed to develop is held adjacent to the color comparator card 10, both of which are held up to the light for a determination of which of the five colors on the card most closely approximates the color development of the test solution. The TPM range for card color selected equates to the TPM concentration of the oil sample.

In methods using an internal reference standard, the support means of the diagnostic testing unit is capable of serving as a spectrophotometry sample cell. The oil sample and testing solution are mixed in the support means according to the method of the present invention and the support means is placed in the sample position of a spectrophotometer. The spectrum of the mixture is then recorded relative to the internal standard. This enables comparison of the spectrum to other standardized spectra and development of a calibration curve for quantitative analysis of an analyte.

The process of the invention has been found to provide results which correlate very well with IUPAC-AOAC methods and methods of the American Oil Chemists Society and other commonly performed tests for assaying oil samples for contaminants or constituents. The invention has been shown to indicate in a reliable manner the state of an oil sample without the need for complex and lengthy laboratory testing.

The diagnostic testing unit of the present invention can be provided in a set including more than one test solution with different indicators providing different ranges over which an oil sample can be assayed for a contaminant or constituent. The different indicators can also be specific to different contaminants or constituents. For example, a test unit can be provided for a high FFA concentration, an intermediate FFA concentration and a low FFA concentration, together with test units for high, intermediate and low concentrations of alkalines and TPM's. In this manner, particular contaminants, constituents and the concentrations thereof of oils can be identified with a set of testing units based upon a common technology.

The testing solution and the diagnostic test units of the present invention can be prepared by means conventional in the art. The method of preparation may vary somewhat depending upon the specific diagnostic test unit to be manufactured, without departing from the essential parameters common to the technology. The indicator is admixed with the vehicle until a uniform mixture is obtained. Optional materials may then be added at this time with mixing continued until a uniform homogeneous mixture is obtained. High melting point materials may be added by either heating the material until it is fluid, or heating the mixture until the high melting point material is incorporated. The material is then layered on or within the support means, sealed and packaged for distribution.

The following examples are given to illustrate the invention, but are not deemed to be limiting thereof. All percentages given throughout the specification are based upon weight unless otherwise indicated.

EXAMPLES

EXAMPLE 1

A test solution for the assay of total polar materials (TPM) was prepared by mixing 0.0075 g FD&C Blue No. 1 dye with 100 g of a 1:1 weight ratio of glyceryl mono-oleate and glyceryl monostearate.

A series of 30 restaurant derived lightly hydrogenated soybean oil samples containing known TPM concentrations were prepared, in which the TPM concentrations increased in increments of 1%. Four milliliters of each oil sample were mixed in a vial with 0.5 milliliter of test solution. The vials were capped and shaken until a homogeneous mixture was obtained. Within 1 minute maximum color development in each sample occurred. The colors of the test solution relative to the TPM concentrations are depicted in Table I.

TABLE I

| Test Solution Color | TPM Concentration |
| --- | --- |
| blue | below 5% |
| blue-green | 5 to 12% |
| light green | 13 to 16% |
| green | 17 to 23% |
| olive green | 24% and above |

Four milliliters of a similarly derived oil sample containing an unknown amount of TPM is mixed in the same manner with 0.5 milliliter of test solution. After shaking and allowing for maximum color development, the color of the test solution corresponded to the green color indicative of a TPM content between about 17 and about 23%.

EXAMPLE 2

A test solution for the assay of free fatty acids (FFA) was prepared as in Example 1, using 0.0250 g bromcresol green as the indicator. To this mixture, 0.1 weight percent of potassium hydroxide was added.

A series of 5 restaurant derived hydrogenated soybean oil samples containing known FFA concentrations were prepared, in which the FFA concentrations increased in increments of 1%. Four milliliters of each oil sample were mixed in a vial with 0.5 milliliter of test solution. The vials were shaken and the color was permitted to develop as in Example 1. The colors of the test solutions relative to the FFA concentrations are depicted in Table II.

TABLE II

| Test Solution Color | FFA Concentration |
| --- | --- |
| blue | below 2% |
| light blue | 2% |
| blue-green | 3% |
| yellow | above 3% |

Four milliliters of a similarly derived oil sample containing an unknown amount of FFA was mixed in the same manner with 0.5 milliliter of the test solution and the color allowed to develop. The color of the test solution corresponded to the blue-green color indicative of a 3% FFA concentration.

EXAMPLE 3

A test solution for the assay of alkaline materials was prepared as in Example 1 using 0.005 g bromphenol blue as the indicator and 100 g glycerol monooleate as the vehicle.

A series of 10 hydrogenated soybean oil samples containing known soap concentrations were prepared in which the soap concentrations increased in increments of 0.1%. Four milliliters of each oil sample was mixed with 0.5 milliliter of test solution, shaken and the color change allowed to develop, as in Example 1. The colors of the test solutions relative to the soap concentrations are depicted in Table III.

TABLE III

| Test Solution Color | Soap Concentration |
| --- | --- |
| yellow | 0% |
| slightly greenish | 0.1% |
| pale blue | 0.3% |

TABLE III-continued

| Test Solution Color | Soap Concentration |
| --- | --- |
| dark blue | 1.0% |

Four milliliters of a similarly derived oil sample containing an unknown soap content were mixed in the same manner with 0.5 milliliter of the test solution and the color allowed to develop. The color of the test solution corresponded to the pale blue color indicative of a 0.3% soap concentration.

EXAMPLE 4

A restaurant frying simulation is performed using electrically-heated small fryers frying a mixture of 75% french fries, 15% breaded chicken and 10% breaded fish as a food mix. Two unsaturated soybean oils having iodine valves (IV) of 102 and 105 respectively, commonly used for the reconstitution of preferred foods were utilized.

The frying history of the two oils are depicted in Table IV, which shows both the total elapsed time the oil spent in the heated fryer, as well as the total elapsed in-use time during which the oil was used to fry food. At regular intervals 4.0 milliliter samples of the oils were mixed with 0.5 milliliter of the test solution from Example 3. The samples were thoroughly mixed, placed in a Sharp Carousel II 650 watt home microwave oven and exposed to microwave energy for a period of five minutes. This exposure was sufficient for each sample to heat the maximum temperature it was capable of developing upon exposure to microwave energy, known as the Curie temperature, which temperatures were measured using a temperature probe.

The temperature profiles of the two sample series are also depicted in Table IV. The oil sample having a 105 IV eventually developed Curie temperatures exceeding 120° C., which resulted in a color development in the test solution. This color development coincided with a fall-off in oil performance. The oil sample having a 102 IV maintained acceptable performance over the time period of the test. The oil never developed a Curie temperature in excess of 110° C. and test solutions mixed with this oil and exposed to microwave energy never exhibited a color change.

TABLE IV

| Total Time | In Use | 102 I.V. Oil | 105 I.V. Oil |
| --- | --- | --- | --- |
| 0 min-Fresh- | 0 min | 100.2° C. | 104.8° C. |
| 1244 | 61 | 99.0 | 112.0 |
| 2174 | 183 | 103.1 | 105.2 |
| 2654 | 226 | 104.0 | 100.0 |
| 3344 | 304 | 108.0 | 108.9 |
| 4690 | 468 | 100.4 | 112.3 |
| 5280 | 612 | 106.0 | 163.8* |
| 5905 | 759 | 104.8 | 144.6* |
| 6600 | 906 | 107.2 | 142.5* |

*Color change development in test solution

The invention being thus described, it will be obvious that the same may be varied in many ways. Such variations are not to be regarded as a departure from the spirit and scope of the invention, and all such modifications are intended to be included within the scope of the following claims.

We claim:

1. A method for the determination in a single phase of the amount of one or more non-triglyceride oil contaminants or constituents selected from the group consisting of oxidatively produced species and condensation products, thermal condensation products, hydrolytic products, aldehydes, ketones, unsaturated materials, water, heavy metals and metal ions, carbohydrates, gossypol, chlorophyll, tocoquinone and proteins, said process consisting essentially of the steps of (a) mixing a predetermined amount of an oil-miscible test solution with a predetermined amount of an oil, said test solution including an oil-miscible vehicle selected from the group consisting of monoglycerides, diglycerides and mixtures thereof, and an indicator deliverable in admixture with said vehicle for assaying said oil contaminants or constituents, wherein said indicator in combination with said oil contaminants or constituents forms a reaction product characteristic of the amount of said oil contaminants or constituents, said indicator and vehicle are present in quantities and at a pH effective to provide detectable quantities of said reaction product, and said indicator is present relative to said vehicle in an amount effective to provide measurable quantities of said reaction product in response to the presence of said oil contaminants or constituents;

(b) agitating said test solution and said oil so that a uniform homogeneous mixture forms and allowing for the development of said reaction product in said mixture; and (c) determining the amount of contaminants or constituents in said oil by comparing said reaction product development to a known standard.

2. The method of claim 1, wherein said vehicle comprises a 1:1 weight ratio of monoglyceride to diglyceride.

3. The method of claim 1, wherein said vehicle consists essentially of glyceryl mono-oleate.

4. The method of claim 1, wherein said indicator is present at a concentration between about 0.001 to 0.10 weight percent.

5. The method of claim 1, wherein said indicator is a mechanical indicator selected from the group consisting of activated carbon, activated minerals, synthetic silica gels, molecular sizing materials and ion exchange materials.

6. The method of claim 1, wherein said reaction product development is a color change and said standard is an external color standard to which said color change is compared.

7. The method of claim 1, wherein said indicator is selected from the group consisting of bromcresol purple and bromthymol blue and said method further includes the step of exposing said homogenous mixture to microwave radiation until the maximum microwave temperature of said mixture is attained prior to comparing said reaction product development to said known standard.

8. The method of claim 1, wherein said vehicle monoglycerides are selected from the group consisting of glyceryl mono-oleate, glyceryl monostearate, glyceryl monolaurate and mixtures thereof and said vehicle diglycerides are selected from the group consisting of glyceryl dioleate, glyceryl distearate, glyceryl dilaurate and mixtures thereof.

9. The method of claim 8, wherein said vehicle comprises a 1:1 weight ratio of glyceryl monooleate to glyceryl monostearate.

10. The method of claim 1, wherein said standard is an internal standard that is compared to said reaction product development spectrophotometrically.

11. The method of claim 10, wherein said internal standard is a dye.

12. The method of claim 1, wherein said test solution further includes a diluent selected from the group consisting of other monoglycerides, other glyceridic esters, paraffinic oils, lipids, one or more fatty oils and natural and synthetic waxes.

13. The method of claim 12, wherein said fatty oil is selected from the group consisting of hydrogenated and partially hydrogenated coconut oil, olive oil, palm oil, peanut oil, rapeseed oil, canola oil, riceseed oil, rice bran oil, soybean oil, cottonseed oil, sunflower oil, safflower oil, sesame oil, tallows, fish oils, poultry oils, fat replacers, and mixtures thereof.

14. The method of claim 12, wherein said natural and synthetic waxes are selected from the group consisting of paraffin wax, petrolatum, polyethylene glycol, polypropylene glycol, microcrystalline wax, beeswax, carnuba wax, candelilla wax, lanolin, bayberry wax, spermaceti, ricebran wax and combinations thereof.

15. The method of claim 1, wherein said indicator is selected from the group consisting of bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol, FD&C Blue No. 1, FD&C Blue No. 2, malachite green, methyl yellow, FD&C Red 40, Congo red, brom-chlorophenol blue, chlorophenol red and salts and lakes thereof.

16. The method of claim 15, wherein said method is for the assay of free fatty acids, said pH is alkaline, and said indicator is selected from the group consisting of bromphenol blue, methyl yellow, congo red, methyl orange, brom-chlorophenol blue, bromcresol green, bromcresol purple and chlorophenol red.

17. The method of claim 16, wherein said indicator is bromcresol green.

18. The method of claim 15, wherein said method is for the assay of alkaline materials, said pH is acidic, and said indicator is selected from the group consisting of bromphenol blue, methyl yellow, congo red, methyl orange, brom-chlorophenol blue, bromcresol green, bromcresol purple and chlorphenol red.

19. The method of claim 18, wherein said indicator is bromphenol blue.

20. The method of claim 15, wherein said method is for the assay of total polar materials and said indicator is selected from the group consisting of bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol, FD&C Blue No. 1, FD&C Blue No. 2 and malachite green.

21. The method of claim 20, wherein said indicator is selected from the group consisting of FD&C Blue No. 1, FD&C Blue No. 2, malachite green and bromcresol green.

22. The method of claim 21, wherein said indicator is FD&C Blue No. 1.

23. A diagnostic test unit for the determination in a single phase of the amount of one or more oil non-triglyceride contaminants or constituents selected from the group consisting of oxidatively produced species and condensation products, thermal condensation products, hydrolytic products, aldehydes, ketones, unsaturated materials, water, heavy metals and metal ions, carbohydrates, gossypol, chlorophyll, tocoquinone and proteins, said test unit consisting essentially of:

(a) an oil-miscible test solution including an oil-miscible vehicle selected from the group consisting of monoglycerides, diglycerides and mixtures thereof, and an indicator deliverable in admixture with said vehicle for assaying said contaminants or constituents, wherein said indicator in combination with said contaminants or constituents forms a reaction product characteristic of the amount of said contaminants or constituents, said indicator and vehicle are present in quantities and at a pH effective to provide detectable quantities of said reaction product, and said indicator is present relative to said vehicle in an amount effective to provide measurable quantities of said reaction product in response to the presence of said oil contaminants or constituents; and (b) a known standard for determining the amount of said contaminants or constituents in said oil by comparison thereto.

24. The diagnostic unit of claim 23, wherein said vehicle comprises a 1:1 weight ratio of monoglyceride to diglyceride.

25. The diagnostic unit of claim 23, wherein said vehicle consists essentially of glycerol monooleate.

26. The diagnostic unit of claim 23, wherein said indicator is present at a concentration between about 0.001 and 0.10 weight percent.

27. The diagnostic unit of claim 23, wherein said indicator is a mechanical indicator selected from the group consisting of activated carbon, activated minerals, synthetic silica gels, molecular sizing materials and ion exchange materials.

28. The diagnostic unit of claim 23, wherein said vehicle monoglycerides are selected from the group consisting of glyceryl mono-oleate, glyceryl monostearate, glyceryl monolaurate and mixtures thereof and said vehicle diglycerides are selected from the group consisting of glyceryl dioleate, glyceryl distearate, glyceryl dilaurate and mixtures thereof.

29. The diagnostic unit of claim 28, wherein said vehicle comprises a 1:1 weight ratio of glyceryl monooleate to glyceryl monostearate.

30. The diagnostic unit of claim 23, wherein said standard is an internal standard that is compared to said reaction product spectrophotometrically.

31. The diagnostic unit of claim 30, wherein said internal standard is a dye.

32. The diagnostic unit of claim 23, wherein said reaction product is a color change and said standard is an external color standard to which said color change is compared.

33. The diagnostic unit of claim 32, further comprising a physical support member for said test solution comprising a polypropylene tube, and said external standard comprises a translucent plastic card printed with translucent color inks, the colors of which equate test solution color to non-triglyceride concentration, which plastic and ink have combined light transmission properties substantially similar to the combined light-transmission properties of said polypropylene tube and said test solution.

34. The diagnostic unit of claim 23, wherein said test solution further includes a diluent selected from the group consisting of other monoglycerides, other glyceridic esters, paraffinic oils, lipids, one or more fatty oils and natural and synthetic waxes.

35. The diagnostic unit of claim 34, wherein said fatty oil is selected from the group consisting of hydrogenated and partially hydrogenated coconut oil, olive oil, palm oil, peanut oil, rapeseed oil, canola oil, riceseed oil, rice bran oil, soybean oil, cottonseed oil, sunflower oil, safflower oil, sesame oil, tallows, fish oils, poultry oils, fat replacers, and mixtures thereof.

36. The diagnostic unit of claim 34, wherein said natural and synthetic waxes are selected from the group consisting of paraffin wax, petrolatum, polyethylene glycol, polyproylene glycol, microcrystalline wax, beeswax, carnuba wax, candelilla wax, lanolin, bayberry wax, spermaceti, ricebran wax and combinations thereof.

37. The diagnostic unit of claim 23, wherein said indicator is selected from the group consisting of bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol, FD&C Blue No. 1, FD&C Blue No. 2, malachite green, methyl yellow, FD&C Red 40, Congo red, brom-chlorophenol blue, chlorphenol red and salts and lakes thereof.

38. The diagnostic unit of claim 37, wherein said method is for the assay of free fatty acids, said pH is alkaline, and said indicator is selected from the group consisting of bromphenol blue, methyl yellow, congo red, methyl orange, brom-chlorophenol blue, bromcresol green, bromcresol purple and chlorophenol red.

39. The diagnostic unit of claim 38, wherein said indicator is bromcresol green.

40. The diagnostic unit of claim 37, wherein said method is for the assay of alkaline materials, said pH is acidic, and said indicator is selected from the group consisting of bromphenol blue, methyl yellow, congo red, methyl orange, brom-chlorophenol blue, bromcresol green, bromcresol purple and chlorophenol red.

41. The diagnostic unit of claim 40, wherein said indicator is bromphenol blue.

42. The diagnostic unit of claim 37, wherein said method is for the assay of TPM's and said indicator is selected from the groups consisting of bromphenol blue, thymol blue, xylenol blue, bromcresol purple, methylene violet, methylene green, methyl orange, methyl red, patent blue, bromthymol blue, bromcresol green, cresolindophenol, triphenol-indophenol, thymolinophenol, FD&C Blue No. 1, FD&C Blue No. 2 and malachite green.

43. The diagnostic unit of claim 42, wherein said indicator is selected from the group consisting of FD&C Blue No. 1, FD&C Blue No. 2, malachite green and bromcresol green.

44. The diagnostic unit of claim 43, wherein said indicator is FD&C Blue No. 1.

45. The diagnostic unit of claim 23, further comprising a physical support member for said test solution comprising a sheet, rod, web, filter, strip, vial or tube.

46. The diagnostic test unit of claim 45, wherein said support member is a tube or vial and said support member further comprises an agitation means selected from the group consisting of a plastic or glass beads, stainless steel balls, pladdles, stir-rods, stir-bars, magnetic stir-bars and ultrasonic susceptors.

47. The diagnostic test unit of claim 45, wherein said support member is a tube or vial sealed with a twist cap or a snap cap.

48. The diagnostic test unit of claim 47, wherein said twist cap or snap cap further comprises a well.

49. The diagnostic test unit of claim 45, wherein one or more surfaces of said test solution are covered by a sealant selected from the group consisting of paraffin wax, microcrystalline wax, natural waxes, synthetic polymers, low molecular-weight monoglycerides and acrylates capable of being cross-linked in situ.

50. The diagnostic test unit of claim 49, wherein said test solution is a first test solution, said test unit further comprises a second test solution, and said sealant provides a barrier between said first and second test solutions.

51. The diagnostic test unit of claim 49, wherein all of said surfaces of said test solution are covered by said sealant.

52. The diagnostic unit of claim 45, wherein said support member comprises a material selected from the group consisting of glass, cellulose, wood, metals, metal oxides, textiles, polymerics and polymeric-ceramic hybrids.

53. The diagnostic unit of claim 52, wherein said polymeric material is selected from the group consisting of polyethylene, polypropylene, polyacrylate, polycarbonates and polymeric fluorocarbons.

54. The diagnostic unit of claim 53, wherein said support member is a polypropylene tube.

55. The diagnostic unit of claim 53, wherein said vial or tube is capable of functioning as a spectrophotometric cell.

56. A method for the single phase assay of an oil, consisting essentially of the steps of:
    (a) mixing a predetermined amount of an oil-miscible test solution with a predetermined amount of said oil, said test solution including an oil-miscible vehicle selected from the group consisting of monoglycerides, diglycerides and mixtures thereof, an enzyme specific to a fatty acid and an indicator deliverable in admixture with said vehicle for assaying said fatty acid, wherein said indicator in combination with said fatty acid forms a reaction product characteristic of the presence of said fatty acid, said indicator and vehicle are present in quantities and at a pH effective to provide detectable quantities of said reaction product, and said indicator is present relative to said vehicle in an amount effective to provide measurable quantities of said reaction product in response to the presence of said fatty acid; and
    (b) agitating said test solution and said oil so that a uniform, homogeneous mixture forms, and allowing said oil and said enzyme to react to produce said fatty acid, and for the development of said reaction product of said fatty acid and said indicator in said mixture; and
    (c) determining the presence or absence of said fatty acid in said oil by comparing said reaction product development to a known standard.

57. The method of claim 56, wherein said enzyme is a lipase enzyme.

58. A diagnostic test unit for the single phase assay of an oil, said test unit consisting essentially of:
    (a) an oil-miscible test solution including an oil-miscible vehicle selected from the group consisting of monoglycerides, diglycerides and mixtures thereof, an enzyme specific to fatty acid, and an indicator deliverable in admixture with said vehicle for assaying said fatty acid, wherein said indicator in combination with said fatty acid forms a reaction product characteristic of the amount of said fatty acid, said indicator and vehicle are present in quantities and at a pH effective to provide detectable quantities of said reaction product, and said indicator is present relative to said vehicle in an amount effective to provide measurable quantities of said reaction product in response to the presence of said fatty acid; and (b) a known standard to determining the presence or absence of said fatty acid in said oil by comparison thereto.

59. A diagnostic unit of claim 58, wherein said enzyme is a lipase enzyme.

* * * * *